(12) United States Patent
Curiel et al.

(10) Patent No.: US 8,932,053 B2
(45) Date of Patent: Jan. 13, 2015

(54) ASSEMBLY FORMED BY A BRACKET, A CLIP AND A BASE FOR AN ORTHODONTIC APPARATUS, AND ORTHODONTIC APPARATUS COMPRISING SAME

(75) Inventors: Patrick Curiel, Neuilly sur Seine (FR); Philippe Salah, Paris (FR); William Ayache, Neuilly sur Seine (FR)

(73) Assignee: American Orthodontics Corporation, Sheboygan, WI (US)

( * ) Notice: Subject to any disclaimer, the term of this patent is extended or adjusted under 35 U.S.C. 154(b) by 0 days.

(21) Appl. No.: 13/997,557

(22) PCT Filed: Dec. 27, 2011

(86) PCT No.: PCT/EP2011/074093
§ 371 (c)(1),
(2), (4) Date: Sep. 3, 2013

(87) PCT Pub. No.: WO2012/089731
PCT Pub. Date: Jul. 5, 2012

(65) Prior Publication Data
US 2013/0337398 A1    Dec. 19, 2013

Related U.S. Application Data

(60) Provisional application No. 61/429,893, filed on Jan. 5, 2011.

(30) Foreign Application Priority Data

Dec. 28, 2010   (FR) ..................................... 10 61309

(51) Int. Cl.
*A61C 7/30* (2006.01)
*A61C 7/28* (2006.01)

(52) U.S. Cl.
CPC . *A61C 7/30* (2013.01); *A61C 7/285* (2013.01); *A61C 7/287* (2013.01)

USPC ................................................ 433/11; 433/10

(58) Field of Classification Search
USPC ......................................................... 433/10, 11
See application file for complete search history.

(56) References Cited

U.S. PATENT DOCUMENTS 4,248,588 A * 2/1981 Hanson ............................ 433/11
4,419,078 A * 12/1983 Pletcher .......................... 433/10

(Continued)

FOREIGN PATENT DOCUMENTS

DE      4407100 A1     9/1995
EP      1234549 A1     8/2002

(Continued)

OTHER PUBLICATIONS

International Search Report, PCT International Application No. PCT/EP2011/074093, mailed Feb. 6, 2012.

*Primary Examiner* — Ralph Lewis
(74) *Attorney, Agent, or Firm* — Andrus Intellectual Property Law, LLP

(57) ABSTRACT

An orthodontic assembly includes a self-ligating attachment having a groove for receiving an orthodontic arch. An elastic clip can be reversibly moved between an open position and a closed position sealing the groove. A base including an external surface and an occlusal surface, said external surface of the base supporting the attachment and said occlusal surface of the base being intended to rest on one of the patient's teeth. The aforementioned clip can be moved in an at least partially rotational manner between the open position and the closed position. Moreover, the area of the above-mentioned base that supports the attachment comprises a depression at least partially in the form of a cup and the clip is inserted into the depression when in the closed position.

16 Claims, 2 Drawing Sheets

(56) References Cited

U.S. PATENT DOCUMENTS

| | | |
|---|---|---|
| 5,474,445 A | 12/1995 | Voudouris |
| 5,562,444 A | 10/1996 | Heiser et al. |
| 5,630,715 A | 5/1997 | Voudouris |
| 5,711,666 A | 1/1998 | Hanson |
| 5,857,850 A | 1/1999 | Voudouris |
| 5,906,486 A * | 5/1999 | Hanson ............... 433/11 |
| 5,913,680 A | 6/1999 | Voudouris |
| 6,071,118 A | 6/2000 | Damon |
| 6,071,119 A | 6/2000 | Christoff |
| 6,168,428 B1 | 1/2001 | Voudouris |
| 6,257,883 B1 | 7/2001 | Voudouris |
| 6,368,105 B1 | 4/2002 | Voudouris et al. |
| 6,939,133 B2 | 9/2005 | Voudouris |
| 7,214,057 B2 | 5/2007 | Voudouris |
| 7,247,019 B2 | 7/2007 | Abels et al. |
| 7,416,408 B2 | 8/2008 | Farzin-Nia et al. |
| 7,442,039 B2 * | 10/2008 | Opin et al. ............... 433/11 |
| 7,611,353 B2 | 11/2009 | Sommer |
| 7,963,767 B2 | 6/2011 | Lewis et al. |
| 2004/0166459 A1 | 8/2004 | Voudouris |
| 2004/0175667 A1 | 9/2004 | Abels et al. |
| 2007/0072143 A1 | 3/2007 | Sommer |
| 2007/0166658 A1 | 7/2007 | Voudouris |
| 2009/0004617 A1 | 1/2009 | Oda et al. |
| 2010/0261131 A1 | 10/2010 | Ruiz-Vela et al. |

FOREIGN PATENT DOCUMENTS

| | | |
|---|---|---|
| EP | 1287789 A2 | 3/2003 |
| WO | 2008044912 A1 | 4/2008 |
| WO | 2010028276 A1 | 3/2010 |
| WO | 2010103178 A1 | 9/2010 |

* cited by examiner

ASSEMBLY FORMED BY A BRACKET, A CLIP AND A BASE FOR AN ORTHODONTIC APPARATUS, AND ORTHODONTIC APPARATUS COMPRISING SAME

CROSS-REFERENCE TO RELATED APPLICATIONS

This application is the U.S. national stage application of International Application PCT/EP2011/074093, filed Dec. 27, 2011, which international application was published on Jul. 5, 2012, as International Publication WO 2012/089731 in the French language. The International Application claims priority of French Patent Application 1061309, filed Dec. 28, 2010.

BACKROUND

The invention relates to a base/bracket assembly to be used in a customized orthodontic apparatus for treating a patient and intended mainly, but not exclusively, to be used in the case of a lingual technique, that is to say with the apparatus located on the non-visible posterior face of the teeth.

Conventionally, such apparatuses comprise:
- at least one orthodontic arch wire, in other words a metal wire which exerts on the teeth a force that tends to move them from their unsatisfactory initial position, known as the "malposition", into a satisfactory final position, known as the "corrected position";
- and a set of brackets which are each provided with at least one groove for holding an orthodontic arch wire.

The brackets are fixed individually to the patient's teeth in a predetermined position that allows the orthodontic arch wire to transfer to the teeth the necessary forces for them to pass from the malposition into the corrected position during the treatment. This fixing is produced by way of a "base", that is to say an intermediate element, one face of which conforms to the surface of the tooth to which the bracket is intended to be fixed, and the other face of which supports the bracket.

Most commonly, one or more orthodontic arch wires, together with a single set of brackets each comprising one or more grooves, are used.

The development of lingual orthodontic techniques, which have the esthetic advantage of leaving the apparatus virtually invisible from the outside, started around 1980. In these techniques, an important element in the success of the treatment is the good positioning of the bracket and of its groove on the tooth, since this positioning determines the orientation of the forces that are imposed on the corresponding tooth and thus the orientation of the tooth in the various spatial directions when it is located in the final corrected position. This positioning is much more difficult to carry out in the lingual technique than in the technique known as labial or vestibular (in which the apparatus is located on the anterior face of the teeth) on account of the great angulation of the posterior faces of the teeth. This angulation means that a small error in the positioning of the bracket can place the groove in an incorrect position which is incapable of correcting the position of the tooth as desired.

IT techniques have been able to bring significant improvements to the ease of designing customized orthodontic apparatuses that are specific to each patient.

In particular, document WO-A-03/068099 teaches designing in a customized manner an assembly formed firstly by the virtual image of a base for fixing to the tooth, designed digitally on the basis of a computer image of the patient's arch with the malpositioned teeth, and secondly by a virtual image of a bracket provided with a groove for the insertion of the orthodontic arch wire, this image being drawn from a virtual library of brackets having predetermined forms. Next, a bracket formed of a single body resulting from the combination of these two images is produced by rapid prototyping. Next, an orthodontic arch wire that is shaped with the aid of a special device and is intended to connect the brackets and to bring the patient's teeth into the corrected position is designed.

Once the orthodontic arch wire has been inserted into the groove in the bracket, this groove is closed off by the practitioner so as to keep the arch wire therein. Most commonly, this closing off is realized by inserting a metal or elastomeric ligature into the groove. However, this method has the drawback of not having optimum reliability on account of the fact that it is possible for the ligature not to be fitted correctly by the practitioner and its properties can change over time, in particular in the case or an elastomeric ligature. If the ligature is displaced or damaged, the patient has to go to the orthodontist's practice in order to have it replaced. Likewise, the desired realization of each ligature takes a great deal of time, and this makes the fitting of the arch wire a lengthy and uncomfortable procedure for the patient. Finally, if, during the course of the treatment, it is necessary to change the arch wire, the orthodontist has to irreversibly destroy the ligatures in order to remove the arch wire, this procedure also being lengthy and uncomfortable for the patient. This step of destroying the ligature also causes the orthodontist to exert forces that are transmitted to the bracket and can weaken its connection to the base.

Considerable progress has been made by using what are known as "self-ligating" brackets. These brackets are designed to hold an elastic (metal) clip which, once the arch wire has been inserted, is placed in a position which closes off the groove and allows the clip to prevent the arch wire from coming out. This placement is generally carried out by sliding the clip in the longitudinal direction of the bracket between a stand-by position leaving the groove open for the insertion of the arch wire and a closed functional position closing off the groove, it being possible for this sliding to be complemented by a rotational movement as in document U.S. Pat. No. 6,776, 613. The clip is moved manually by the orthodontist using one of his usual tools and takes only a fraction of a second. Similarly, the disengagement of the clip prior to changing the arch wire is carried out by simply pulling in the opposite direction to the previous sliding and is just as quick. Finally, the mechanical and dimensional characteristics of the metal clip are stable over time and if the bracket and the clip are produced with good dimensional precision, the functionality and reliability of the ligature are satisfactory.

However, the known self-ligating brackets also have their drawbacks. They are often more bulky than ordinary brackets, and thus more problematic for the patient, on account of the fact that the longitudinal sliding movement of the clip has to be able to take place over a certain travel. Above all, this sliding movement can be hampered if tartar has built up on the bracket because it has not been removed by proper brushing of the apparatus in the mouth by the patient. When the arch wire is changed, the opening and replacement of the clip are thus made more difficult and one of the advantages of self-ligating brackets is at least partially lost.

Another drawback with the known self-ligating brackets, in which the clip is moved by sliding between its open position and its closed position and vice versa, is the following.

It is advantageous for the bases to be as thin as possible in order that the overall space requirement in terms of height of the base/bracket assembly is as small as possible, so as to limit discomfort for the patient. To this end, consideration can be given to manufacturing a base the thickness of which decreases with respect to its nominal thickness (which is usually around 0.4 mm) in the region which supports the bracket. In the support region, it would be good to be able to decrease the thickness of the base to about 0.1 mm, knowing that a saving of 0.3 mm over the thickness of the base/bracket assembly for all the assemblies mounted on the treated arch already appreciably increases comfort for the patient.

However, as will be seen hereinbelow, it is not possible to limit oneself to reducing this thickness of the base in this support region. Specifically, it has to be possible to slide the clip over a certain rectilinear travel in order to be able fit it and take it out, and this requires that a clear space be provided to this end over a sufficient length in front of the bracket. The thinned part of the base should thus then have a large surface and this would weaken the base in a prohibitive manner.

BRIEF DISCLOSURE

The aim of the invention is to provide orthodontists with an assembly formed by a self-ligating bracket, the clip closing the groove in the bracket and the base on which the bracket is fitted, the configuration of which substantially reduces the maximum thickness of the assembly without preventing the clip from moving and without significantly affecting the strength of the base.

To this end, one subject of the invention is an assembly intended to be part of an orthodontic apparatus and comprising:
- a self-ligating bracket, said bracket having in its longitudinal direction an outer face and an occlusal face and being provided on its outer face with a groove for holding an orthodontic arch wire;
- an elastic clip that can be moved in a reversible manner between an open position, leaving a free passage for the insertion of the arch wire into the groove or the extraction of the arch wire from the groove, and a closed position closing off the groove;
- and a base having an outer face and an occlusal face, said outer face of the base supporting said bracket and said occlusal face of the base being intended to rest on a patient's tooth by conforming to the surface of said tooth; characterized in that said clip can be moved in an at least partially rotary movement between its open position and its closed position, and in that said base comprises, in the region where it supports the bracket, an at least partially dish-shaped depression, the clip being inserted into said depression when it is in the closed position.

The clip may foe moved between said positions substantially by a rotational movement, without the clip sliding in rectilinear translation.

The clip may foe moved between said positions substantially by a rotational movement, with the clip then sliding in rectilinear translation or vice versa.

The clip may be U-shaped over at least a part of its length.

The depression in the base may have on its bottom a protrusion intended to support the bracket.

The depression in the base may have on its bottom a protrusion intended to support the bracket.

The assembly may be intended for an orthodontic apparatus of the lingual type.

The assembly may be intended for an orthodontic apparatus of the vestibular type.

One subject of the invention is an orthodontic apparatus comprising an orthodontic arch wire and assemblies which each comprise a bracket, a clip and a base that are each intended to be fitted to a patient's tooth, characterized in that at least one of said assemblies is of the above type.

As will have been understood, the invention is based on a novel design of the assembly formed by a self-ligating bracket, the clip which closes off its groove and the base which supports the bracket. Firstly, the clip has a curved shape, for example a U-shape, over a part or all of its length, and this enables it to move over the bracket by executing a rotational movement. The base, of which the nominal thickness is in accordance with the usual standards, has a depression in the form of a dish in the region supporting the bracket, and thus a progressive and only localized reduction in the thickness, with the result that overall its strength is not affected with respect to the case where it has the usual constant thickness. During the closing operation of the clip, a terminal part of the clip is housed in the depression, under the body of the bracket, which has an opening to this end.

BRIEF DESCRIPTION OF THE DRAWINGS

The invention will be understood better from reading the following description, with reference to the following appended figures, in which.

DETAILED DISCLOSURE

Figure 1:
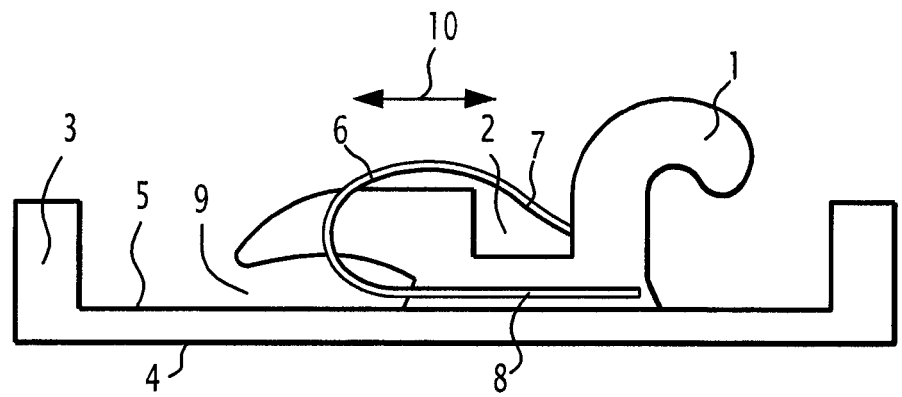
FIG. 1 schematically shows a longitudinal section through a fictitious bracket/clip/base assembly not in accordance with the invention, implementing the principle of a base provided with a depression but making use of a clip that is moved purely in translation.
Figure 2:
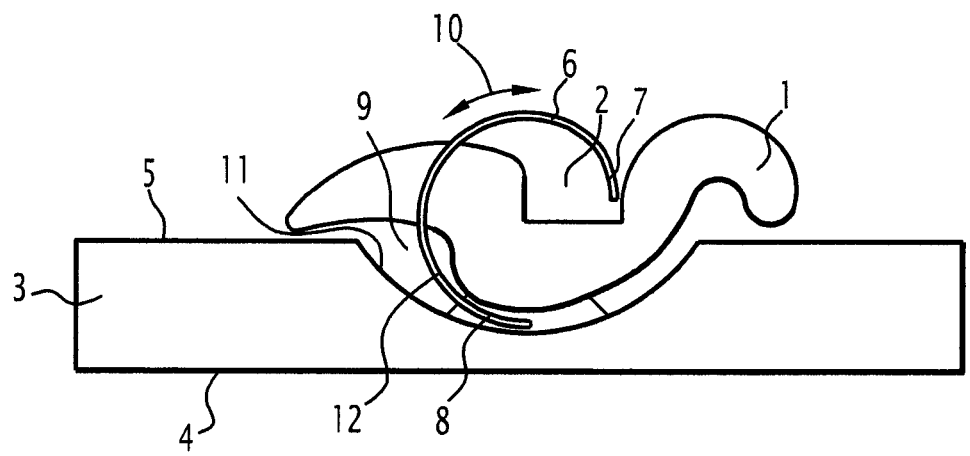
FIG. 2 schematically shows a longitudinal section through an example of a bracket/clip/base assembly in accordance with the invention.

The terms "horizontal" and "vertical", which will be employed in the rest of the description, will be used with reference to FIGS. 1 and 2 and to the position that the devices shown occupy therein, but it will be obvious for a person skilled in the art to transpose these terms to other positions of the devices.

In the fictitious assembly in FIG. 1, which is not in accordance with the invention and is only illustrated to show that all the elements which will be mentioned below as part of the invention are indeed indispensable, the following elements are noted:
- a bracket 1 comprising on its outer face a groove 2 for the insertion of an orthodontic arch wire (not shown);
- a base 3, the occlusal face 4 of which is intended to be fixed to a lingual or vestibular face of a patient's tooth, and the outer face 5 of which carries the bracket 1;
- and an elastic clip 6 which is generally U-shaped in the example shown, a first arm 7 of which can close off the groove 2 and the second arm 8 of which is housed between the base 4 and the bracket 1 when the groove 2 is closed off, as shown in FIG. 1.

The bracket 1 is placed on the base 3 in a depression 9 in order that the maximum overall height of the base/bracket assembly is as small as possible.

It can be seen that, in order to move the clip 6 in translation between its open and closed positions in the directions of the arrow 10, sufficient space has to be available in front of the bracket 1. This is only possible if the depression 9 has a dimension that largely exceeds that of the bracket 1. The consequence of this is that the thickness of the base 3 is considerably reduced over a large portion of the surface of the base 3. It passes, for example, from a value of 0.4 mm to a value of 0.1 mm. This causes the base 3 to be excessively fragile.

The invention remedies this problem by providing that the bracket 1 and the clip 6 have forms such that the movements of the clip 6 during the closing and opening operations of the groove 2 are rotational movements over at least a part of the travel of the clip 6, or even preferably over the entirety of this travel, as in the example schematically illustrated in FIG. 2. The path of the arm 8 of the clip 6 which passes between the base 3 and the bracket 1 is thus curved, and this makes it possible for the depression 9 formed in the base 3 to at least partially have the form of a dish, that is to say to have a wall 11 which has a curvature that follows the travel of the clip 6 as closely as possible during its movements. In this manner, as can be seen in FIG. 2, it is possible to limit the volume of the depression 9 containing the bracket 1 to a minimum, with a reduction in the thickness of the base 3 from for example 0.4 mm to 0.1 mm which is both progressive and localized. The weakening of the strength of the base 3 on account of the presence of the depression 9 is thus reduced to its very minimum. It is also possible to shape the lower part of the bracket 1 such that it follows the curvature of the dish. Of course, the regions of the depression 9 that cannot interfere with the movements of the clip 6 can have any desired form, the essential feature being that it is possible to place the bracket 1 in the depression 9 in order to reduce the space requirement in terms of height of the bracket 1/base 3 assembly.

All this means that, with respect to conventional configurations or to the fictitious configuration in FIG. 1, it is possible to reduce the overall space requirement in terms of height of the bracket 1/clip 6/base 3 assembly by virtue of the depression 9 without otherwise compromising the strength of the base 3. The apparatus thus becomes more comfortable for the patient to wear, while preserving excellent reliability.

As an alternative with respect to the example shown, it may be possible to provide that the clip 6 be able to move partly in rectilinear translation. It would then be necessary to provide a depression 9 having a different form, the wall 11 of which would be parallel to the direction of translation of the clip 6, and the advantages obtained with respect to a configuration in which the path of the clip 6 is purely rotational would be somewhat diminished. Nevertheless, the increase in comfort for the patient and in the strength of the base 3 would still be significant with respect to the configuration exemplified in FIG. 1, all the more so since the direction of translation does not have to be horizontal: the principle of a reduction that is progressive and as localized as possible in the thickness of the base 3 in the depression 9 is thus retained.

Figure 3:
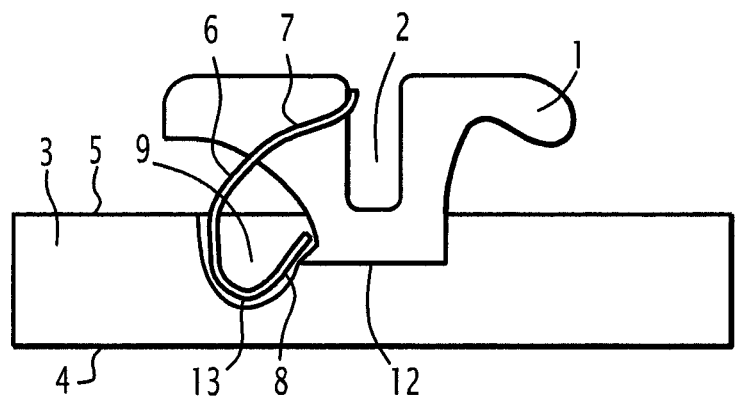
FIG. 3 schematically shows a longitudinal section through another example of a bracket/clip/base assembly in accordance with the invention with the clip in the open position.
Figure 4:
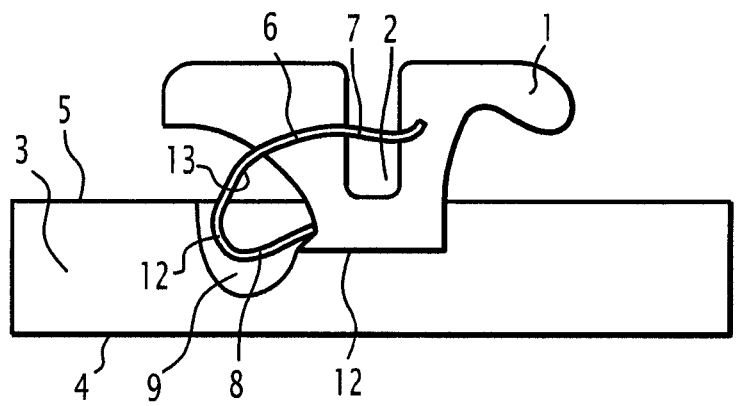
FIG. 4 shows the same assembly with the clip in the closed position.

FIGS. 3 and 4 show a variant of the invention which makes the deepest part of the depression 9 even more localized. The depression 9 has on its bottom a protrusion 12 on which the bracket 1 is placed. It can be seen in FIG. 3 that when the clip 6 is in the open position, the top 13 of its curvature is received at the bottom of the depression 9, and thus has a height that is lower than that of the protrusion 11 on which the bracket 1 rests. In FIG. 4, the assembly is shown with the clip 6 in the closed position. In this variant, on account of the presence of the protrusion 12, the reduction in thickness of the bracket 1/clip 6/base 3 assembly is, for equal thicknesses of the bracket 1 and the base 3, less than in the case in FIG. 2. However, this configuration further reduces the part of the depression 9 where the base 3 has a large reduction in its thickness, and a stronger base 3 is obtained. Of course, the principle of this variant can foe applied to an assembly in which the clip moves partly in rectilinear translation.

The design and production of the base 3 of the assembly according to the invention are carried out by computer aided design and computer aided manufacturing means that are conventionally used.

The invention can be used both for apparatuses of the lingual type and for apparatuses of the vestibular type.

The invention claimed is:

1. An assembly intended to be part of an orthodontic apparatus and comprising:
    a self-ligating bracket, said bracket having in its longitudinal direction an outer face and an occlusal thee and being provided on its outer face with a groove for holding an orthodontic arch wire;
    an elastic clip that can be moved in a reversible manner between an open position, leaving a free passage for the insertion of the arch wire into the groove or the extraction of the arch wire from the groove, and a closed position closing off the groove; and
    and a base having an outer face and an occlusal face, said outer face of the base supporting said bracket and said occlusal face of the base being intended to rest on a patient's tooth by conforming to the surface of said tooth, the base comprises an at least partially dish-shaped depression and the bracket is secured to the base in the depression;
    wherein the clip can be moved in an at least partially rotary movement between the open position and the closed position, the clip being at least partially located in said depression when the clip is in the closed position.

2. The assembly as claimed in claim 1, characterized in that it comprises means such that the clip is moved between said positions substantially by a rotational movement, without the clip sliding in rectilinear translation.

3. The assembly as claimed in claim 1, characterized in that it comprises means such that the clip is moved between said positions substantially by a rotational movement, with the clip then sliding in rectilinear translation or vice versa.

4. The assembly as claimed in claim 1, characterized in that the clip is U-shaped over at least a part of its length.

5. The assembly as claimed in claim 1 further comprising, a protrusion extending from a bottom of the depression in the base, the protrusion-supports the bracket.

6. The assembly as claimed in claim 1 wherein the orthodontic apparatus is configured to be mounted to a lingual surface of a tooth.

7. The assembly as claimed in claim 1 wherein the orthodontic apparatus is configured to be mounted to a vestibular surface of a tooth.

8. An orthodontic apparatus comprising:
    an orthodontic arch wire; and
    a plurality of assemblies, each assembly fitted to a. tooth of the dentition of a patient and configured to receive the orthodontic arch wire, each assembly comprising:
        a self-ligating bracket, said bracket having in its longitudinal direction an outer face and an occlusal face and being provided on its outer face with a groove for holding an orthodontic arch wire;
        an elastic clip that can be moved in a reversible manner with at least partially rotary movement between an open position, leaving a free passage for the insertion of the arch wire into the groove or the extraction of the arch wire from the groove, and a closed position closing off the groove; and a base having an outer face and an occlusal face, the outer face of the base supporting the bracket and the occlusal face of the base being configured to rest on a patient's tooth by conforming to the surface of said tooth, the base comprises an at least partially dish-shaped depression, the bracket secured to the base in the depression, and the clip is at least partially located in the depression when the clip is in the closed position.

9. The orthodontic apparatus of claim 8 wherein the bracket secured to the base in the depression reduces an overall a height of the assembly.

10. The orthodontic apparatus of claim 8, wherein the depression in the base is at least partially defined by a curved wall which progressively extends into the base, and the clip at least partially follows the curved wall as the clip moves between the open position and the closed position.

11. The orthodontic apparatus of claim 10, wherein the base further comprises a protrusion within the depression, the protrusion interior the base from the outer face and the bracket is secured within the depression to the protrusion.

12. The orthodontic apparatus of claim 11 wherein a bottom of the depression is interior the base from the outer face and the protrusion.

13. The orthodontic apparatus of claim 10, wherein the clip follows the curved wall of the depression between the bracket and the base as the clip moves between the open position and the closed position.

14. A self-ligating bracket assembly, comprising:
a bracket having an outer face and an occlusal face, the bracket further comprising a groove in the outer face configured to receive an orthodontic arch wire;
a clip that comprises a first arm and a second arm and the elastic clip is rotatively moveable in a reversible manner between an open position wherein the groove is free of obstruction to receive the orthodontic arch wire and a closed position wherein the groove is closed off by the first arm of the clip; and
a base having an outer face and an occlusal face, the occlusal face being configured to conform to a surface of a tooth of a patient, and a depression extending into the base from the occlusal face, wherein the occlusal face of the bracket is secured to the base in the depression and the second arm of the clip passes between the bracket and the base as the clip moves between the open position and the closed position.

15. The self-ligating bracket assembly of claim 14, wherein the depression is at least partially defined by a curved wall which progressively extends into the base from the outer face of the base, and the clip at least partially follows the curved wall as the clip moves between the open position and the closed position.

16. The self-ligating bracket assembly of claim 15, wherein the base further comprises a protrusion within the depression, the protrusion interior the base from the outer face of the base and the bracket is secured to the protrusion.

* * * * *